United States Patent [19]

Aoki et al.

[11] Patent Number: 5,721,215
[45] Date of Patent: Feb. 24, 1998

[54] INJECTABLE THERAPY FOR CONTROL OF MUSCLE SPASMS AND PAIN RELATED TO MUSCLE SPASMS

[75] Inventors: Kei Roger Aoki, Laguna Hills; Larry A. Wheeler, Irvine; Michael E. Garst, Newport Beach, all of Calif.

[73] Assignee: Allergan, Waco, Tex.

[21] Appl. No.: 619,780

[22] Filed: Mar. 20, 1996

[51] Int. Cl.⁶ .......................... A61K 38/16; A61M 13/00
[52] U.S. Cl. .................. 514/21; 514/2; 604/51; 128/898
[58] Field of Search .................. 514/2, 21; 604/51; 128/898

[56] References Cited

U.S. PATENT DOCUMENTS 5,401,243   3/1995   Borodic ........................ 604/51

OTHER PUBLICATIONS

Doggrell Journal of Pharmaceutical Methods vol 10(4): pp. 243–254 (1983).
Ishikawa et al Brain Research vol 346(1): pp. 82–88 (1985).

*Primary Examiner*—Stephen Walsh
*Assistant Examiner*—Daryl A. Basham
*Attorney, Agent, or Firm*—Walter A. Hackler

[57] ABSTRACT

A method for administration of botulinum toxin, includes the steps of (a) selecting at least one neuromuscular blocking agent having a duration of activity shorter than neuromuscular blocking activity of botulinum toxin; (b) selecting at least one muscle of a muscle group; (c) intramuscularly injecting the selected agent into the selected muscle; (d) observing muscle relaxation in both the selected muscle and other nonselected muscles in the muscle group to determine spill-over, muscle tone and balance; (e) repeating steps (b)–(d) until a final muscle selection is found; and (f) intramuscularly injecting botulinum toxin into the final muscle selection.

18 Claims, 12 Drawing Sheets

INJECTABLE THERAPY FOR CONTROL OF MUSCLE SPASMS AND PAIN RELATED TO MUSCLE SPASMS

The present invention relates to an improved method for the administration of botulinum toxin and to the use and selection of neuromuscular blocking agents having a duration of activity shorter than the meuromuscular blocking activity of botulinum toxin.

Botulinum toxin is a neurotoxin produced by the bacterium Clostridium botulinum, of which there are seven subtypes: A–G, and has a molecular weight of 150,000. This toxin binds to haemagglutinin and other nontoxic proteins to form a much bigger molecular complex.

A bacterial toxin, botulinum toxin, in particular botulinum toxin type A, has been used in the treatment of a number of neuromuscular disorders and conditions involving muscular spasm; for example, strabismus, blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in local paralysis and hence relaxation of the muscle afflicted by spasm.

For one example of treating neuromuscular disorders, see U.S. Pat. No. 5,053,005 to Borodic, which suggests treating curvature of the juvenile spine, i.e., scoliosis, with an acetylcholine release inhibitor, preferably botulinum toxin A.

For the treatment of strabismus with botulinum toxin type A, see Elston, J. S., et al., *British Journal of Ophthalmology*, 1985, 69, 718–724 and 891–896. For the treatment of blepharospasm with botulinum toxin type A, see Adenis, J. P., et al., *J. Fr. Ophthalmol.*, 1990, 13 (5) at pages 259–264. For treating squint, see Elston, J. S., *Eye*, 1990, 4(4):VII. For treating spasmodic and oromandibular dystonia torticollis, see Jankovic et al., *Neurology*, 1987, 37, 616–623.

Spasmodic dysphonia has been treated with botulinum toxin type A. See Blitzer et al., *Ann. Otol. Rhino. Laryngol*, 1985, 94, 591–594. Lingual dystonia was treated with botulinum toxin type A according to Brin et al., *Adv. Neurol.* (1987) 50, 599–608. Finally, Cohen et al., *Neurology* (1987) 37 (Suppl. 1), 123–4, discloses the treatment of writer's cramp with botulinum toxin type A.

The term botulinum toxin is a generic term embracing the family of toxins produced by the anaerobic bacterium Clostridium botulinum and, to date, seven immunologically distinct neurotoxins serotype have been identified. These have been given the designations A, B, C, D, E, F and G. For further information concerning the properties of the various botulinum toxins, reference is made to the article by Jankovic and Brin, *The New England Journal of Medicine*, Vol. 324, No. 17, 1990, pp. 1186–1194, and to the review by Charles L. Hatheway in Chapter 1 of the book entitled *Botulinum Neurotoxin and Tetanus Toxin*, L. L. Simpson, Ed., publishes by Academic Press Inc. of San Diego, Calif., 1989, the disclosures in which are incorporated herein by reference.

Botulinum toxin is obtained commercially by establishing and growing cultures of C. botulinum in a fermenter and then harvesting and purifying the fermented mixture in accordance with known techniques.

Botulinum toxin type A, the toxin type generally utilized in treating neuromuscular conditions, is currently available commercially from several sources; for example, from Porton Products Ltd. UK, under the trade name "DYSPORT," and from Allergan, Inc., Irvine, Calif., under the trade name BOTOX® Botulinum Toxin Type A purified complex.

The injection of botulinum toxin into an affected hyperactive muscle results in the selective weakening of that muscle alone. The accuracy of placement of the injection may be improved by the use of electromyographic (EMG) assistance. In this method, the toxin is injected down a hollow EMG electrode, the electrode first having been used to locate the hyperactive muscle or part of the muscle. This technique has been shown both to improve the results of treatment and to reduce the incidence of side-effects.

The paralysis produced by the injections is of a variable degree, depending on the does of toxin used and the size of the muscle, larger muscles requiring larger doses. The onset time is typically between two and five days, peaking in effect a 7–14 days, and the duration of the effect is normally about three months. Even after return of muscle tone there may be a further prolonged effect for some time due to the muscle wasting that had resulted from the disuse of the muscle. Thus the injection usually needs to be repeated every four to six months for the therapeutic effect to be maintained over a prolonged period. The treatment can be repeated indefinitely.

In view of the slow onset time it is desirable to administer the Botulinum accurately and be able to identify proper placement of the injection before actual injection. The present invention is directed toward such a procedure and to the evaluation and selection of neuromuscular blocking agents suitable for use in the administration of Botulinum toxin and separately on short term muscle relaxants.

SUMMARY OF THE INVENTION

In accordance with the present invention, a method for administration of botulinum toxin includes the steps of selecting at least one neuromuscular blocking agent having a duration of activity shorter than the muscular blocking activity of botulinum toxin. Thereafter at least one muscle is selected from a muscle group and the selected agent is intramuscularly injected thereinto. Observation of muscle relaxation in both the selected muscle and other nonselected muscles in the muscle group is made to determine spill-over cover muscle tone and balance.

The injection of selected muscles and observation of relaxation is repeated until a final muscle selection is found. Thereafter botulinum toxin is intramuscularly injected into the other muscle selection. In this manner intramuscular blocking agent having a duration of activity shorter than that of botulinum toxins are utilized to not only identify and select muscles for injection of botulinum toxin, but to ensure proper placement of the injection inward at the later onset and the affects of botulinum toxin, which last for many days, is efficiently injected and accordingly enhances the longer term effect of the botulinum toxin.

More particularly, the method in accordance with the present invention may utilize vecuronium or erabutoxin-b or combinations of both.

Still more particularly the step of selecting at least one narrow muscular blocking agent in accordance with the present invention may include the step of stimulating a group of muscles in the laboratory animal with electrical pulses to induce spasm therein, and thereafter intramuscularly injecting a selected muscle of the muscle group of the laboratory animal with a proposed agent.

Observation is then conducted with regard to reduction in spasm of the injected selected muscle of the laboratory animal as well as observing a reduction in spasm of nonselected muscles of the muscle group of the laboratory animal and thereafter comparing the observations to determine spill-over effects from the injected muscle to non-injected muscles.

The present invention provides an administration method for patients that may be suffering from any condition which compromises neuromuscular function. These conditions can be detected under the procedures of the present invention before injection of botulinum toxin to which the patient may show an exaggerated response.

BRIEF DESCRIPTION OF THE DRAWINGS

The advantages and features of the present invention will be better understood by the following description when considered in conjunction with the accompanying in which.

DETAILED DESCRIPTION

Figure 1A:
FIGS. 1A–1E illustrate the results of intravenous administration of vecuronium ($\mu g\ kg_{-1}$) in soleus and tibialis anterior, curve A showing heart rate bradycardia produced vagal stimulation every 100 seconds curve B with induced spasms shown in the soleus muscle, curve C, in the tibialis anterior muscle shown in curve D, stimulated at 0.1 Hz and nictitating membrane, curve E, stimulated preganglionically every 100 seconds.
Figure 1B:
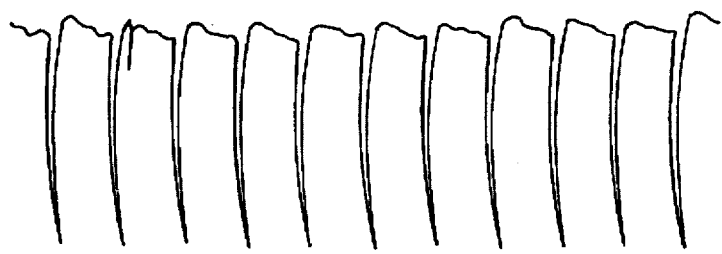
Figure 1C:
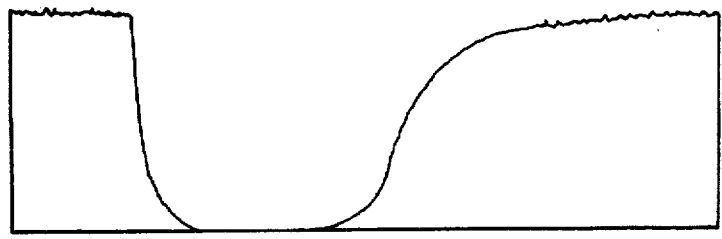
Figure 1D:
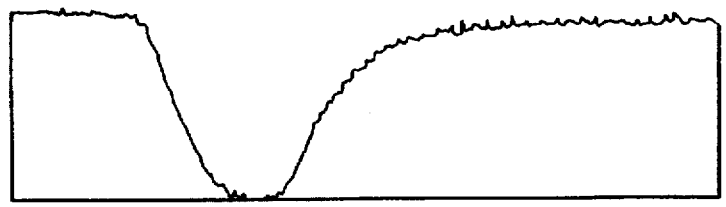
Figure 1E:
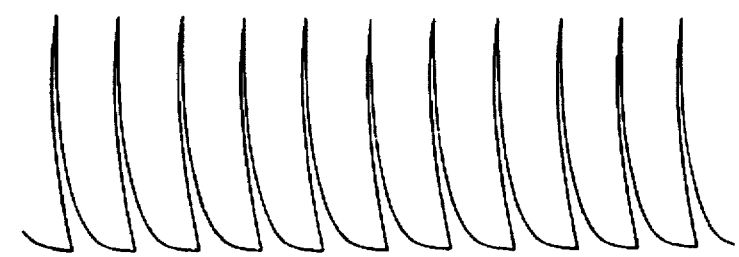

A wide range of protein toxins may be utilized in the present method for example, those listed in Table 1 which lists toxins effective in local therapy along with site of Action Relative to Neuromuscular Junction (NMJ) and Pharmacological Class.

In particular certain studies and data presented herein are utilized protein toxins from snakes which are irreversible blockers of nicotinic muscle-type receptors, such as vecuronium, Erabutoxin-b and lignocaine. In general, after the selection of a proper toxin such as the hereinabove referenced snake toxins which have a duration of activity shorter than the neuromuscular blocking activity of the botulinum toxins the selected shorter activity toxin is injected into the selected muscle of a patient and muscle relaxation in both the selected muscle and other nonselected muscles to determine spill-over muscle tone and balance. When the placement of the toxin is so determined botulinum toxin is then injected for the treatment of the patient in an amount of botulinum toxin and type is that typically the use for therapeutic treatment as is well known in the art.

The present invention is not directed to the quantity or type of botulinum toxin utilized but rather to a method of administering to a patient in a precise manner that amount known to be effective in the art.

As hereinafter discussed in greater detail a number of stimulation protocols have been analyzed including slow and rapid single shocks and intermittent brief tetani with rapid (1 Hz) single shock stimulation found most effective in detecting the effects of the agents herein described. Erabutoxin-b is an irreversible competitive nicotinic antagonist while vesamicol is an inhibitor of vesicular acetylcholine storage.

TABLE 1

| Compound | Site of Action Relative to NMJ | Pharmacological Class |
|---|---|---|
| Acetylcholine Esterase Inducers | Synaptic | ACh Esterase Inducers |
| Aconitine | Presynaptic | Sodium Channel Activator |
| Adenoregulin (from the frog *Phyllomedeusa bicolor*) | Presynaptic | Adenosine Receptor Regulator |
| Adenosine Agonist | Pre & Post Synaptic | Adenosine |
| Adenosine Antagonist | Pre & Post Synaptic | Adenosine |
| Adenosine Regulating Agent | Pre & Post Synaptic | Adenosine |
| Adrenergics | Presynaptic | Alpha Adrenergic |
| Anatoxin-A | Postsynaptic | AChR Agonist |
| Antiepileptics | CNS | Antiepileptics |
| Antisense | Pre & Post Synaptic | Antisense technology for specific proteins or messages important in neurotransmitter release, receptor production. |
| Anxiolytics | CNS | Anxiolytics Antiepileptic |
| Atacurium | Postsynaptic | AChR Antagonist Nondepolarizing muscle relaxant |
| Atracurium besylate (Tracurium) | Postsynaptic | AChR Antagonist Nondepolarizing muscle relaxant |
| Baclofen (Lioresal ®, Geigy; Intrathecal, Medtronic Neurological; generic, Athena, Biocraft, Warner Chilcott) | Presynaptic | GABA analog |
| Bacterial, Plant and Fungal Products | | |
| Batrachotoxin | Presynaptic | Sodium Channel Activator |

TABLE 1-continued

| Compound | Site of Action Relative to NMJ | Pharmacological Class |
|---|---|---|
| Benzylpiperidines | Synaptic Cleft | ACh Esterase Inhibitors (nontraditional) |
| Botanical Neurotoxins | Pre and Post Synaptic as well as Synaptic Cleft | varies |
| Bungarotoxin-β (β-BuTX) | Presynaptic | PLA2 and voltage sensitive potassium channel blocker. Snake toxin from Bungarus multicinctus. |
| Bupivacain | Pre and Post Synaptic | Local Anesthetic Myotoxin |
| Captopril (Capoten ®, Squibb; Capzide ®, Squibb) | Presynaptic | Antihypertensive ACE Inhibitor zinc endopeptidase inhibitor |
| Choline acetyl transferase inhibitors | Pre Synaptic | CAT Inhibitors |
| Cholinesterase Inhibitors | Synaptic Cleft | ACh Esterase Inhibitors |
| Ciguatoxins | Presynaptic | Sodium Channel |
| Conotoxin MI (alpha Conotoxin) | Postsynaptic | AChR Antagonist |
| Conotoxin-μ GIIIA (mu-CT) | | Na+ channel blocker |
| Conotoxin-Ω GVIA (omega-CT) | | Ca2+ channel blocker in neutrons only |
| Curare | Postsynaptic | AChR Antagonist Nondepolarizing |
| Dantrolene Sodium (Dantrium, P & G) | Postsynaptic | Skeletal Muscle Relaxant |
| Dauricine | Post Synaptic | AChR antagonist |
| Decamethonium Bromide | Presynaptic | Ganglionic blocker |
| Dendrotoxin | Pre and Post Synaptic | Potassium Channel blocker |
| Diaminopyridine (3-DAP) | Presynaptic | Botulinum toxin intoxication Reversal |
| Diazepam | CNS | Anxiolytic |
| Doxacurium chloride (Nuromax ®, Burroughs Wellcome) | Postsynaptic | AChR Antagonist Nondepolarizing muscle relaxant |
| Doxorubicin (Adriamyocin, Adria; Rubex, Immunex; Cetus Onoclogy) | Postsynaptic | Myotoxin Chemo Myectomy |
| Epibatidine Dihydrochloride | Postsynaptic | AChR Agonist |
| Felbamate (Felbatol, Carter-Wallace lic to Schering-Plough) | Presynaptic CNS | Antiepileptic |
| Foroxymithine | Presynaptic | Angiotensin I Converting Enzyme inhibitor |
| Gabapentin (Neurontin, Parke-Davis) | Presynaptic CNS | Antiepileptic GABA Analog |
| Gallamine | Postsynaptic | AChR Antagonist |
| Grayantoxin | Presynaptic | Sodium Channel Activator |
| Hexahydroazepinyl Acetamides and other chemical classes | Presynaptic | ACh Releaser |
| Huperzine A | Synaptic Cleft | ACh Esterase Inhibitor |
| Insect Venoms | | |
| Ion Channel Blockers | Pre and Post Synaptic | Channel Blockers |
| Ion Channel Stimulants | Pre and Post Synaptic | Channel Stimulants |
| Latrotoxin-α | Presynaptic | Calcium Ionophore black widow spider venom |

TABLE 1-continued

| Compound | Site of Action Relative to NMJ | Pharmacological Class |
|---|---|---|
| Lidocaine, procaine, mepivacain, etc. | Presynaptic | component Local Anesthetics |
| Linopirdine (DuP 996, Dupont Merck) | Presynaptic | ACh Release Enhancer |
| Lophotoxin and analogs Marine Natural Products | Postsynaptic | AChR Antagonist Irreversible |
| Methocarbamol (Robaxin, Robins Co.) | | CNS Depression, muscle relaxation. |
| Methyllycaconitine | | |
| Mivacurium chloride (Mivacro ®, BW-BW1090U, Burroughs Wellcome) | Postsynaptic | AChR Antagonist Nondepolarizing muscle relaxant |
| Modified Clostridial Toxins | Pre Synaptic | ACh Release Inhibitor |
| Monoclonal antibodies against NMJ components | | receptor, agrin, neurotransmitters, plasma membrane components, inactivating enzymes, etc. |
| Muscarinic Agonist and Antagonists | Pre and Post Synaptic, CNS | Muscarinic Agonist Antagonist |
| Neosaxitoxin Neosurugatoxin | Presynaptic | Sodium Channel Blocker Autonomic Ganglionic AChR Blocker. (no effect @ NMJ) |
| Neuromuscular Blocking Agents | Postsynaptic | AChR Antagonists AChR Depolarizing |
| Neurotoxins from reptile, insects, and other sources | Pre and Post Synaptic as well as Synaptic Cleft | varies |
| Pancuronium Bromide (Organon) | Postsynaptic | AChR Antagonist Nondepolarizing muscle relaxant |
| Pancuronium-3-OH metabolites (Organon) | Postsynaptic | AChR Antagonist Nondepolarizing muscle relaxant |
| Papverine HCl (30 mg/ml) | | Smooth Muscle Relaxants |
| Physostigmine and Analogs | Synaptic Cleft | ACh Esterase inhibitor |
| Pipercuronium (Arduan, Organon) | Postsynaptic | AChR Antagonist Nondepolarizing muscle relaxant |
| Presynaptic Nerve Terminal Recpetors | Pre Synaptic | any extra or intraneuronal recpetors on nerve terminal |
| Short Neurotoxin alpha | Postsynaptic | AChR Antagonist |
| β-Bungarotoxin (β-BuTX) | Presynaptic | Snake toxin from Bungarus multicinctus. |
| Succinylcholine chloride (Anectine, Burroughs Wellcome) | Postsynaptic | AChR Receptor Agonist Depolarizing skeletal muscle relaxant |
| Tetanus Toxin Tetanus Toxin Transporter | Presynaptic Presynaptic | EAA release inhibitor |
| Tetrahydroamino-acridine (THA) | Synaptic Cleft | ACh Esterase Inhibitor |
| Tetrodoxtoxin | Pre and Post Synaptic | Sodium Channel Blocker |
| Tiagabine (Novo Nordisk) | CNS | Antiepileptic GABA uptake inhibitor |
| Transglutaminase inhibitors or induction prevention | Pre and Post Synaptic | Enzyme |
| Valium | | diazepam CNS Anxiolytic |
| Vecuronium (Norcuron, Organon) | Postsynaptic | AChR Antagonist Nondepolarizing muscle relaxant |
| Vecuronium-3-OH metabolites (Organon) | Postsynaptic | AChR Antagonist Nondepolarizing muscle relaxant |
| Veratridine | Presynaptic | Sodium Channel Activator |
| Vigabatrin (Sabril, Marion Merrell Dow) | Presynaptic CNS | Antiepileptic GABA metabolism inhibitor (irreversible) |
| Vesamicol and other drugs with the same mechanism. | Presynaptic | ACh Vesicle transport inhibitor |
| Zinc Endopeptidase and other proteases delivered by Botulinum toxin or tetanus toxin transporter | Pre Synaptic | Enyzmes. reduce neurotransmitter release |

METHODS

Experiments were carried out on cats of either sex anaesthetized with a mixture of α-chloralose (80 mg kg$^{-1}$) and pentobarbitone sodium (5 mg kg$^{-1}$) injected intraperitoneally. Animals were ventilated with room air at the rate of 26 breaths per minute using a tidal volume of 13 ml kg$^{-1}$. The left and right hind limbs were immobilized by drills inserted into the ankle and knee joints. The contractile responses of the tibialis anterior and soleus muscles to stimulation of the sciatic nerve were recorded. The sciatic nerve was stimulated at rates from 0.1 Hz–200 Hz using rectangular pulses of 0.2 ms duration and of a strength greater than that required to produce a maximal twitch. Arterial blood pressure was recorded from the carotid artery using a Statham PC45 pressure transducer. The blood pressure pulse was used to trigger a cardiotachograph to display the heart rate. In some experiments both vagus nerves were ligated and, at 100s intervals, the right vagus nerve was stimulated with 10s duration trains at a frequency of 2–5 Hz and with pulses of 0.5 ms duration and strength greater than that required to produce a maximal reduction in heart rate. Contractions of the nictitating membrane were evoked every 100s by preganglionic stimulation of the cervical sympathetic nerve with 10s duration trains at a frequency of 5 Hz and of strength to produce maximal contractions of the nictitating membrane. Contractile responses of muscles were recorded using Grass FT03C and FT10C force displacement transducers. All responses were displayed on a Grass model 5 ink writing oscillograph.

RESULTS AND DISCUSSION

Figure 2:
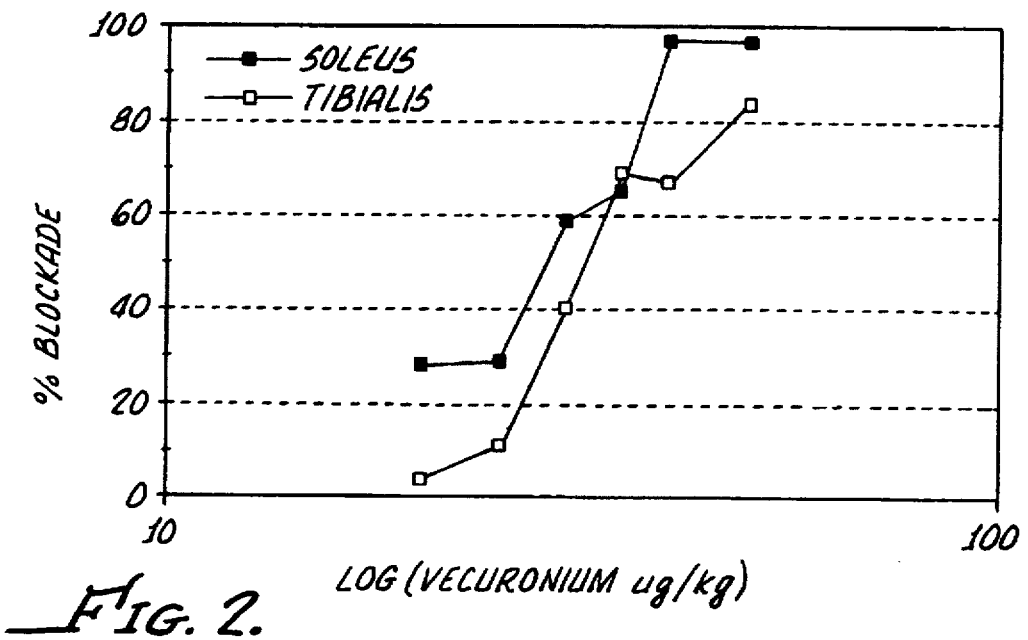
FIG. 2 are representative dose inhibition curves for the intravenous administration of vecuronium on the soleus and tibialis muscles.

The effects of reversible competitive inhibitors by the intravenous and intramuscular routes Initial experiments were designed to compare the potencies of reversible competitive neuromuscular blocking drugs by the intravenous and intramuscular routes. In the case of intravenous administration (FIGS. 1 and 2), vecuronium was administered by bolus injections at 1 hour intervals. The $ED_{50}$ value on the soleus muscle was 36±9 µg kg$^{-1}$ (n=5) and on the tibialis anterior muscle was 40±7 µg kg$^{-1}$ (n=5).

These values closely compare to those obtained previously in the laboratory using these preparations.

Intramuscular injection of vecuronium was made into the central portion of the belly of the tibialis anterior muscle which was being stimulated at 0.1 Hz via the sciatic nerve. The local effects in the tibialis muscle were compared with systemic effects on the ipsilateral soleus muscle. The effects of vecuronium by the intramuscular route were small, variable, and not obviously dose-dependent. Attempts were made to obtain better block by injecting into different areas of the muscle, including in one cat, 3 injections virtually simultaneously into different areas. None of these attempts were successful. Examination of the nervous supply to the muscle demonstrated the diffuse nature of the innervation to different parts of this large muscle mass.

Doses of between 20 and 100 µg of vecuronium were injected intramuscularly with a maximum block of around 25% of tibialis twitch height being achieved. The blocks produced were of long duration (several hours), showing little or no signs of recovery towards control levels (FIG. 3). At the lowest levels of block produced, around 5%, the fastest recovery time observed was 1 hour. This compares with a 10–15 minute total duration of action of vecuronium on the tibialis muscle after intravenous injection (FIG. 1).

Overspill of the vecuronium from the site of intramuscular injection into the general circulation was assessed from the responses of the ipsilateral soleus muscle, stimulated through a common sciatic nerve electrode. Overspill, like the neuromuscular block produced, was variable, but was more obviously dose-related. Thus, at the smaller doses employed (20–50 µg), virtually no spillover was seen (FIG. 3). In one experiment in which 100 µg vecuronium was injected i.m., a maximum long-lasting block of 25% was produced in the injected muscle; in the soleus muscle a block of 60% was produced which took 8 minutes to reach maximal effect and which wore off within 25 minutes. In another experiment in which three doses of vecuronium (50 µg each) were given in rapid succession, greater block was seen in the non-injected tibialis muscle (FIG. 4).

The most extreme example of spillover, was seen in one experiment in which three successive doses of 200 µg of vecuronium were injected i.m. into the tibialis muscle, i.e. a total of 600 µg (200 µg kg$^{-1}$ based on total cat body weight; or 120 mg kg$^{-1}$ based on tibialis anterior weight of approx. 5 g). In this cat a maximum block of 60% was observed on the tibialis muscle, but a complete block was seen on the soleus muscle (FIG. 5). This was in accord with the effects of vecuronium intravenously administered in the same cat. The block on the tibialis muscle developed later than that on the soleus muscle, and the blocks of the muscles began to wear off in 20 minutes in the tibialis muscle and 30 minutes for the soleus muscle. The relatively small block, given the massive dose injected, and the relatively short duration of action, suggest that, although the blocks seen were likely due to spillover into the venous circulation rather than to a local effect, a substantial proportion of the huge dose injected must be retained within a depot store in the injected muscle.

The effects of snake α-toxins by the intramuscular route

Two postjunctionally active snake α-neurotoxins were employed, erabutoxin-b, a relatively short-chain toxin derived from Laticauda semifasciata, and a longer chain toxin derived from Naja naja siamensis (Toxin-3). In these experiments with snake α-toxins, responses from both tibialis anterior muscles were recorded; the injected muscle and the contralateral muscle which served as a control for assessment of spillover.

Two experiments were performed with siamensis toxin-3. In one experiment the first injection of toxin produced a small amount of block in the injected muscle, but there was some evidence of spillover into the general circulation as slight block was observed in the non-injected contralateral tibialis. Further injections showed marked evidence of spillover. In the second experiment siamensis toxin-3 produced no measurable effects at all despite repeated intramuscular injections into different areas of the muscle.

Intramuscular injection of erabutoxin-b proved to be the most successful of any of the drugs tested. Most experiments were performed using this toxin alone, or in combination with vesamicol (see later section).

Figure 7:
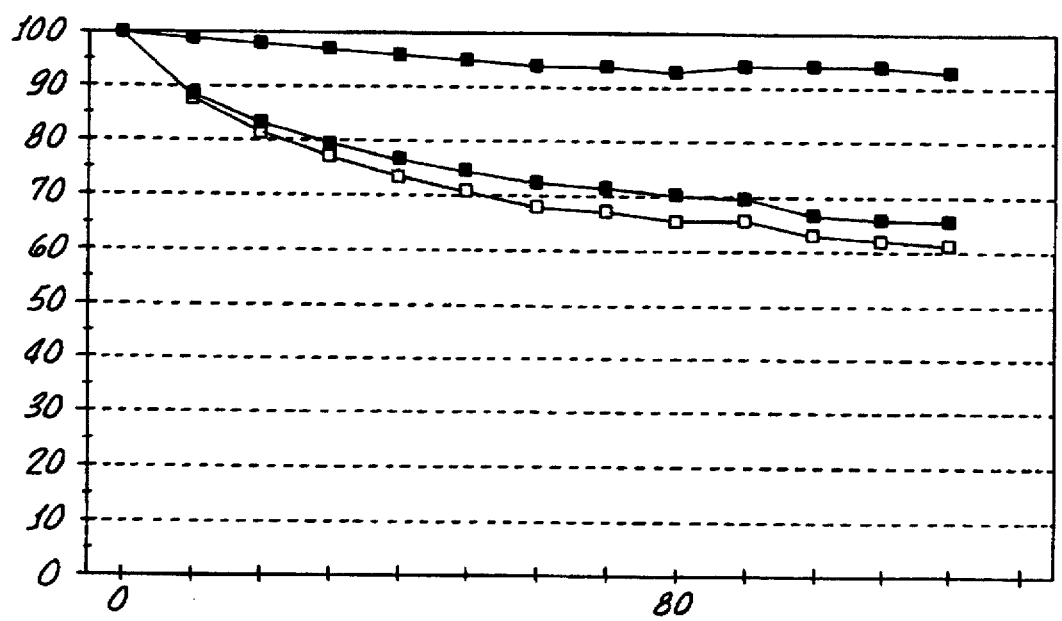
FIG. 7 is a plot of time inhibition for erabutoxin-b in three different cats at 0.1 Hz stimulation frequency in which the percentage control twitch height is shown on the vertical axis and time and minutes on the horizontal axis which shows, in the bottom line block in the injected muscle with the upper line showing rejection and twitch tension in the non-injected muscle and the middle line representing the block in the injected muscle corrected for the diminution of twitch tension in the non-injected muscles.
Figure 3A:
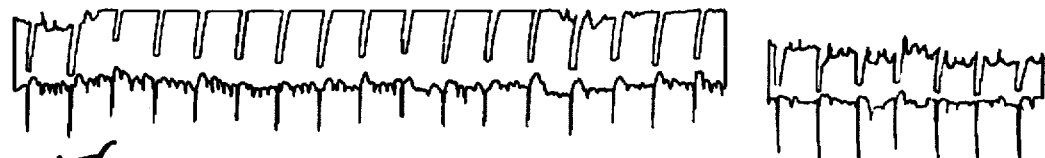
FIGS. 3A–3E are similar to FIGS. 1A–1E with the vecuronium injected at 50 $\mu g\ kg^1$ into the tibialis interior muscle at the point marked, the gap between the panels representing 10 minutes.
Figure 3B:
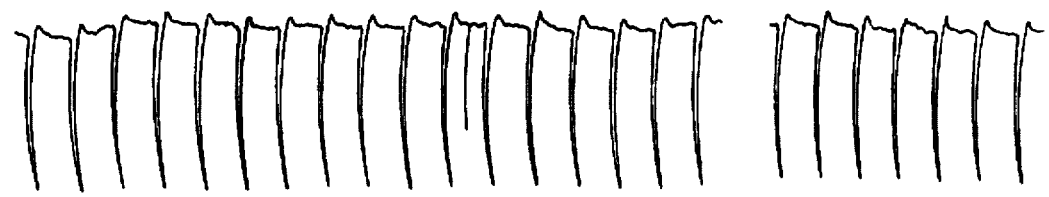
Figure 3C:
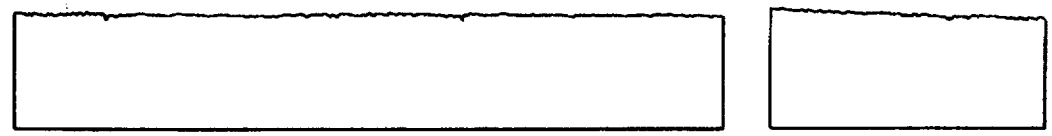
Figure 3D:
Figure 3E:
Figure 4A:
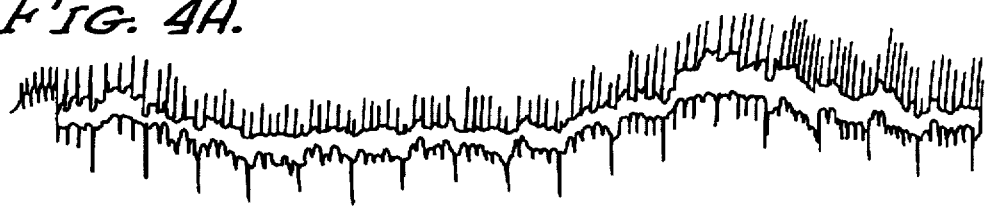
FIGS. 4A–4D represent three injections of vecuronium (50 mg) made in rapid succession to different parts of the belly of the tibialis interior muscle at the arrow, Curves A, B, C, and D being identified as FIGS. 1A–1D.
Figure 4B:
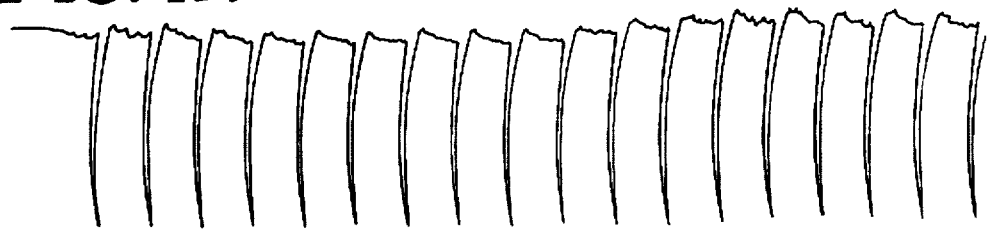
Figure 4C:
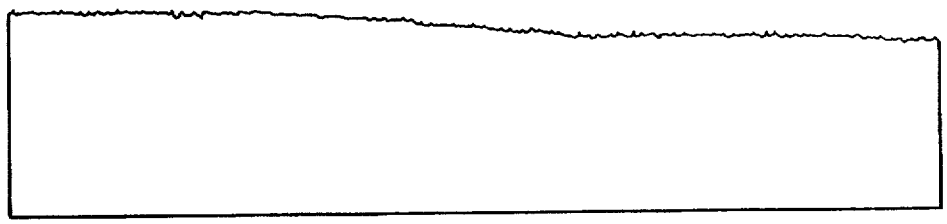
Figure 4D:
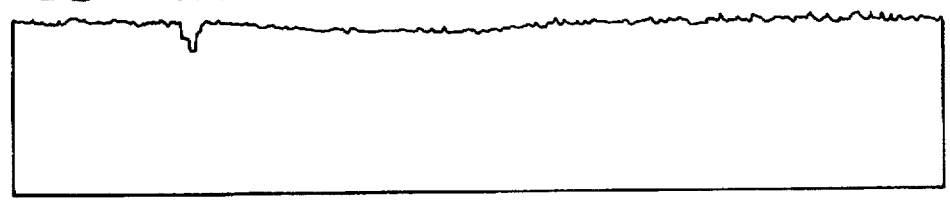
Figure 5A:
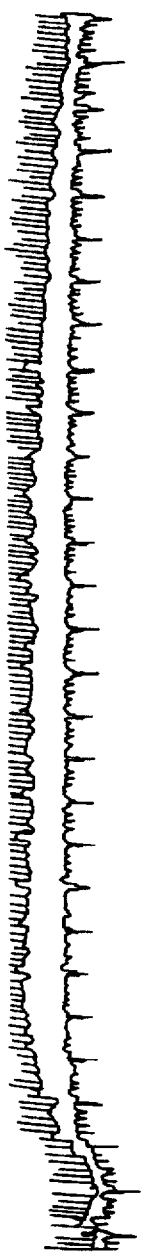
FIGS. 5A–5D are similar to FIG. 4A–4D showing three injections of vecuronium and 200 $\mu g$ at the arrow and showing that the block develops more rapidly in the non-injected soleus muscle (c) than in the injected tibialis muscle (d)
Figure 5B:
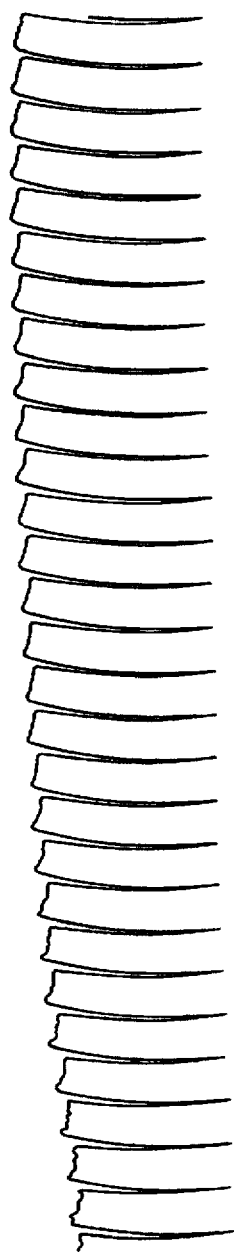
Figure 5C:
Figure 5D:
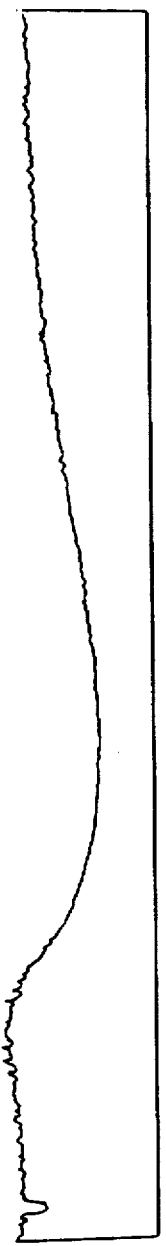
Figure 6A:
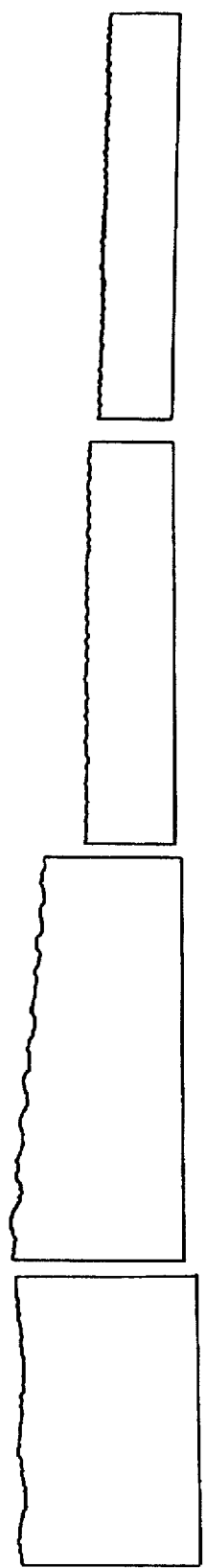
FIGS. 6A–6B represent muscle block achieved through the intramuscular injection of erabutoxin-b in which the tibialis anterior muscle was injected at the arrow shown in Curve A and the contralateral uninjected tibialis interior muscle, Curve B were recorded, the arrow indicating an injection of 0.2 mg of erabutoxin-b and the time gaps between the third and fourth panel representing 60 minutes.
Figure 6B:
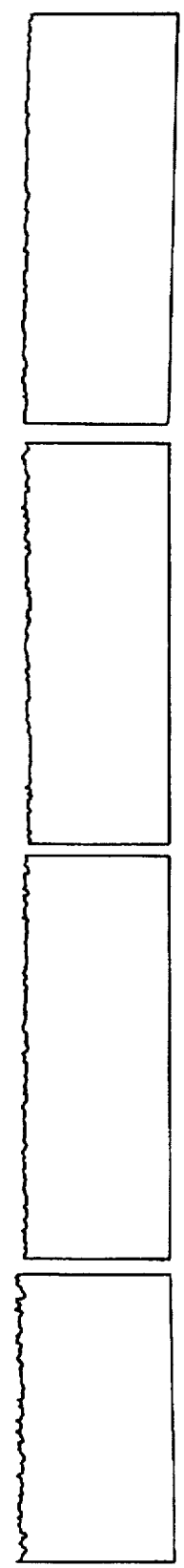

In the experiments using erabutoxin-b alone, 0.2 mg of the toxin was injected. Stimulation rate was 0.1 Hz. In four experiments erabutoxin-b produced a very slow developing block in the injected muscle (FIGS. 6 and 7). There was no evidence of block in the contralateral tibialis muscle, indicating lack of significant spillover into the general circulation. The maximum level of neuromuscular block achieved ranged from 25–60% block. The maximum block was achieved in 1½–2 hours and stabilized thereafter. In 3 of the cats the block was monitored for 4 hours after injection; in only one animal was there a small amount of recovery; in the other two the block showed no signs of recovering from its plateau level.

The lack of spillover into the general circulation was confirmed in one cat in which no recovery had been seen in the injected muscle 4 hours after injection. In this cat 0.2 mg erabutoxin-b was injected i.m. into the contralateral muscle. The rate of development of block was similar to that seen in the previously injected muscle 4 hours earlier. This suggested that no erabutoxin-b was present at sub-blocking concentrations in the general circulation i.e. the safety factor in transmission had not been reduced.

The effects of intravenous erabutoxin-b were tested in one cat which had previously received two injections of erabutoxin-b into the same tibialis anterior muscle. Erabutoxin-b (0.2 mg i.v.) had no measurable effect on either the partially blocked previously injected muscle, or on the unaffected contralateral muscle; 0.5 mg erabutoxin-b i.v. produced complete block of both muscles with 5 minutes.

Snake α-toxins are highly specific for acetylcholine receptors at the neuromuscular junction. It was therefore not surprising that no effects attributable to the toxin were observed on responses of tissues to autonomic stimulation. The lack of spillover into the general circulation would also be expected to be a contributing factor to the lack of autonomic actions.

Overall, the effects of erabutoxin-b were promising, with consistent effects on injection and a long-lasting block being produced. Legal considerations made it impossible to follow the block for more than the four hours reported. The lack of spillover effect could be due to a genuine binding of the toxin to sites within the muscle itself, or to destruction of the small amounts of peptide that might have entered the bloodstream.

The effects of an inhibitor of acetylcholine storage by the intramuscular route

The rationale for the use of vesamicol (2-[4-phenylpiperidino] cyclohexanol), an inhibitor of acetylcholine storage by cholinergic synaptic vesicles, is that the action of the compound is highly frequency dependent. Thus, rapid stimulation in the presence of vesamicol leads to a depletion of stores of acetylcholine and the eventual failure of transmission. However, it should be borne in mind that vesamicol, at higher doses and in the few in vivo experiments that have been reported, possesses some other effects including postjunctional block and local anaesthetic activity; the two effects may be related.

For the experiments with vesamicol the tibialis anterior muscles of both legs were stimulated at 1 Hz.

Under this stimulation pattern the twitch tension takes some considerable time to stabilize even in the absence of drugs. Thus, approximately 1 hour was allowed to elapse after setting up the recording until drugs were injected; this stimulation protocol was utilized in subsequent experiments.

Figure 8A:
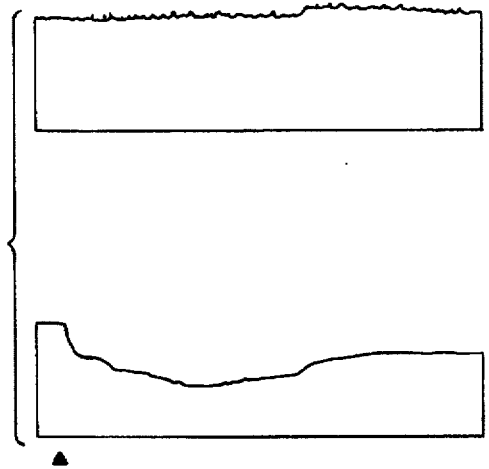
FIGS. 8A–8C are representations of the results of the inner muscular injection of both vesamicol and lignocaine in which both the tibialis anterior muscles were stimulated at 1 Hz and the agents injected at the arrows with Curve A showing the effects of the initial injection of the vesamicol at 3 mg, Curve B showing for comparison the effects of injection of 0.1 ml of a 2% solution of lignocaine (this injection was made 5 hours of the initial dose of vesamicol of at the end of the experiment), Curve C showing the effects of a second dose of vesamicol (3 mg) injected 2½ hours after the first dose, the time gap as shown in Curve C of being fifteen minutes.
Figure 8B:
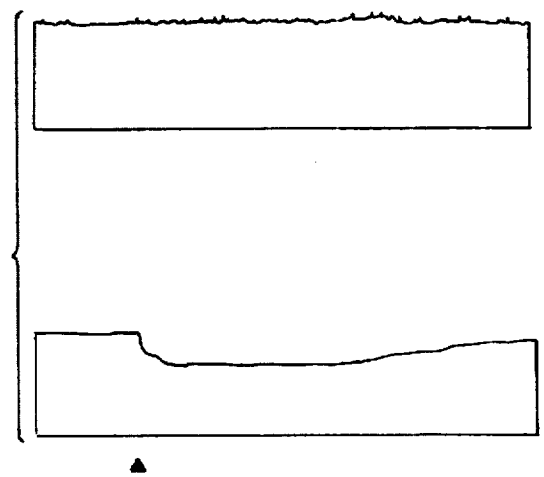
Figure 8C:
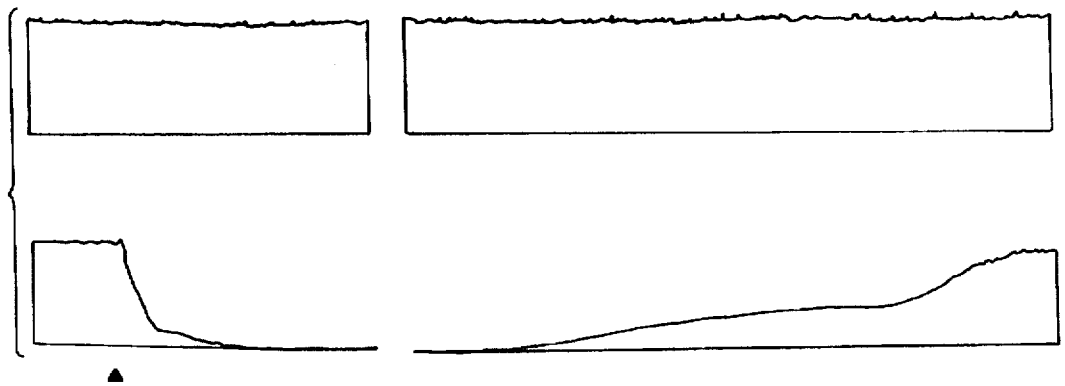

Vesamicol (3 mg) i.m. produced an immediate effect in the injected muscle (FIG. 8), with no effect on the contralateral muscle. Approximately 50% block was achieved on the first injection with full recovery in around 10–15 mins. Given the very rapid effect of vesamicol and its short duration of action, neither of which are consistent with its known effect on acetylcholine storage, a second injection was made into the previously injected muscle, 2 hours after full recovery of twitch height from the first injection. This second injection produced a biphasic block, both in onset and offset characteristics (FIG. 8). The initial effect of the injection was rapid, similar to that of the first dose. However, this rapid onset, immediate effect was followed by a more slowly developing block of the type normally associated with inhibition of acetylcholine metabolism. Block of 100% was achieved. After 30 mins recovery commenced at a gradual rate, followed by a faster rate of recovery. The total duration of the effect was 1¼–1½ hours. No spillover effect was observed during this long-lasting block produced by the second injection of vesamicol into a muscle previously injected with vesamicol.

The biphasic effect of vesamicol suggested that more than one mechanism was involved. One possibility was that the local anaesthetic effect of vesamicol was responsible for the rapid onset, relatively short duration block. This possibility was confirmed by the i.m. injection of lignocaine.

Like the first injection of vesamicol, lignocaine (2 mg) produced an immediate, relatively short-lasting block with no spillover effect (FIG. 8). There was no secondary slow onset of neuromuscular block. It is therefore concluded that the secondary, longer lasting neuromuscular block produced by vesamicol is likely to reflect the action of the compound on acetylcholine storage. The lack of secondary, slow block on the first injection probably indicates that, with this dose, acetylcholine release has not fallen below the threshold required for the endplate potentials to trigger muscle action potentials in all the fibres.

The effects of changes in stimulation frequency on neuromuscular block produced by intramuscular injection Given the fact that the rationale for intramuscular injection is to specifically affect muscles that are firing rapidly, a small number of experiments were carried out using short intermittent tetanic rather than continuous single shock stimulation. Thus, the sciatic nerve was stimulated at 200 Hz for 150 ms every 10 sec. Using this stimulation pattern erabutoxin-b (0.2 mg) produced negligible effects and it was therefore considered that this type of stimulation offered no advantage over single shock stimulation at 0.1 or 1 Hz. The lack of advantage of the tetanic stimulation protocol was confirmed in one experiment using intravenously injected vecuronium where there was little difference in the sensitivity of the tibialis anterior muscle to vecuronium at 0.1 Hz continuous stimulation and at 200 Hz intermittent tetanic stimulation.

Figure 9:
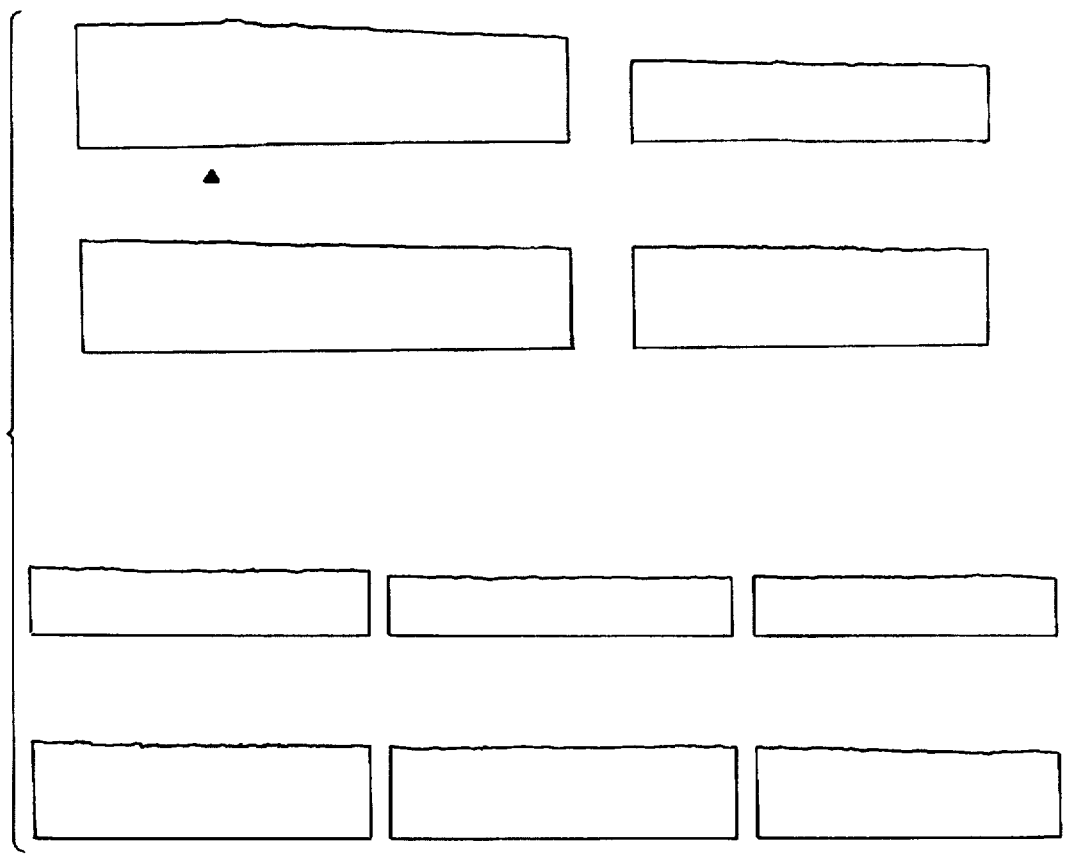
FIG. 9 shows the results due to intramuscular injection of erabutoxin-b in which both tibialis interior muscles were stimulated at 1 Hz and erabutoxin-b at 0.2 mg was injected into the muscle in the upper trace at the arrow, at the time gaps between the records representing 45 minutes and the total time of exposure to erabutoxin-b was 4 hours.
Figure 10:
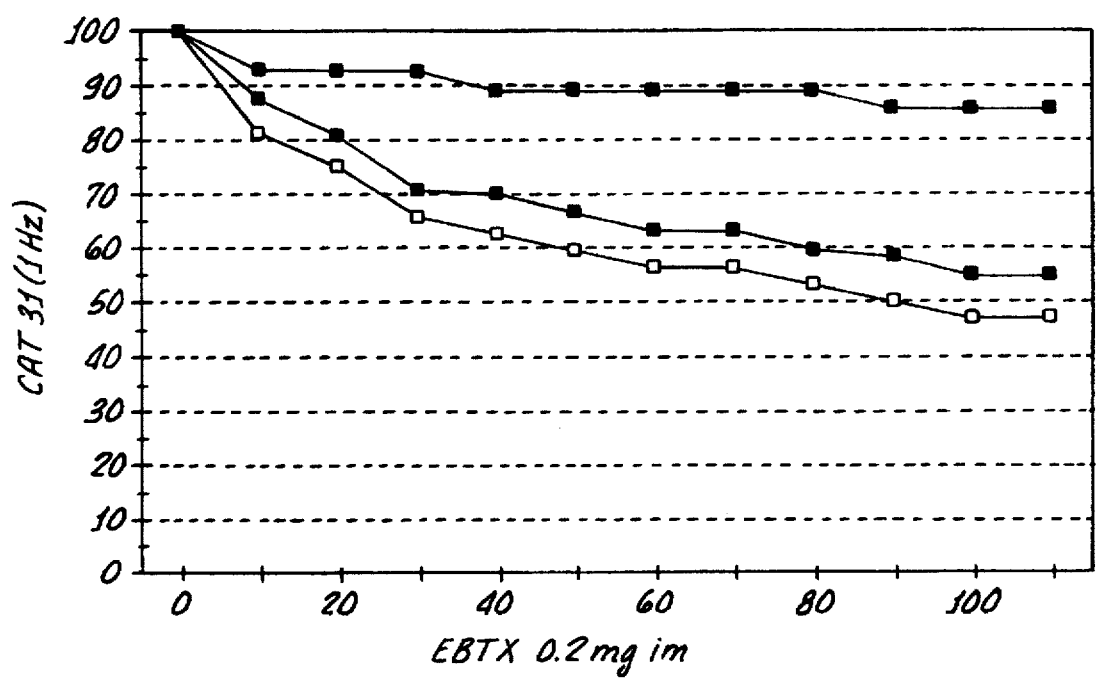
FIG. 10 is a plot of time/inhibition for erabutoxin-b in the experiment shown in FIG. 8 with the percentage control twitch height shown on the vertical axis and time in minutes on the horizontal axis, bottom line showing the block in the injected muscle, the upper line showing the reduction in twitch tension in the non-injected muscle and the middle line representing the block in the injected muscle corrected for the diminution of twitch tension in the non-injected muscle.
Figure 11A:
FIGS. 11A–11E diagram the innermuscular injection of erabutoxin-b and vesamicol combination in which responses of both the soleus and, curve A tibialis anterior muscles are stimulated and 1 Hz, blood pressure vagal, Curve B, soleus, curve C, and tibialis, curve D, and nictating membrane, Curve E responses also being shown in this plot, the paper speed is doubled compared to that shown in FIGS. 1–10 with the left panel showing injection of erabutoxin-b at 0.1 mg at the arrow, second panel vesamicol and 1 mg injected at the arrow with the time between the two injections of 16 minutes and the times between the second and third and third and the fourth panels being 10 and 15 minutes, respectively.
Figure 11B:
Figure 11C:
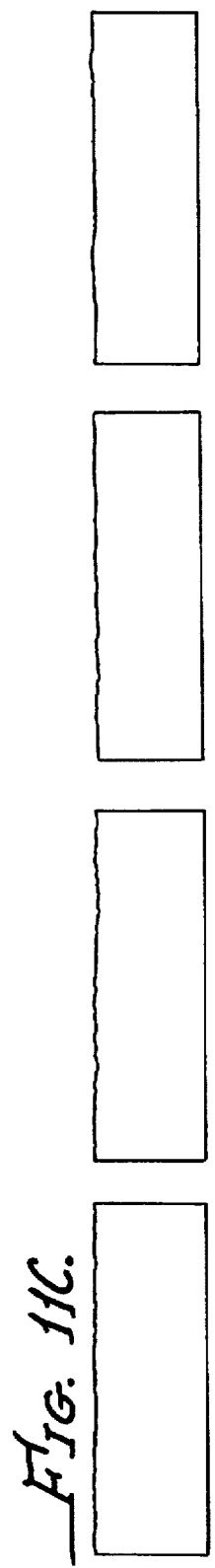
Figure 11D:
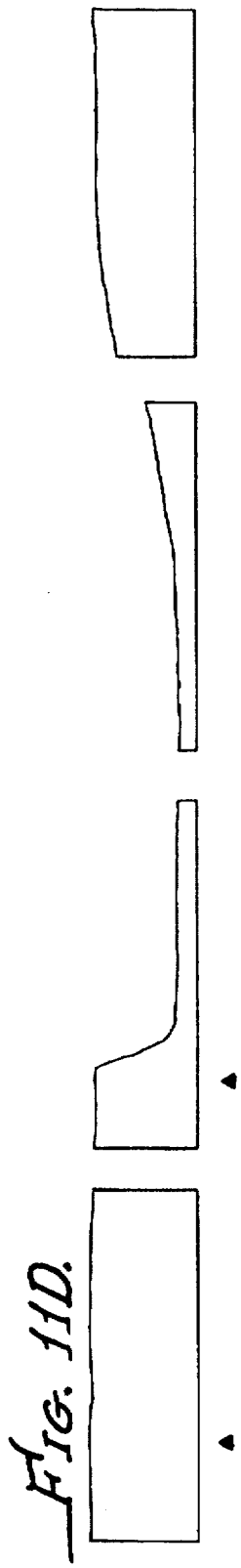
Figure 11E:
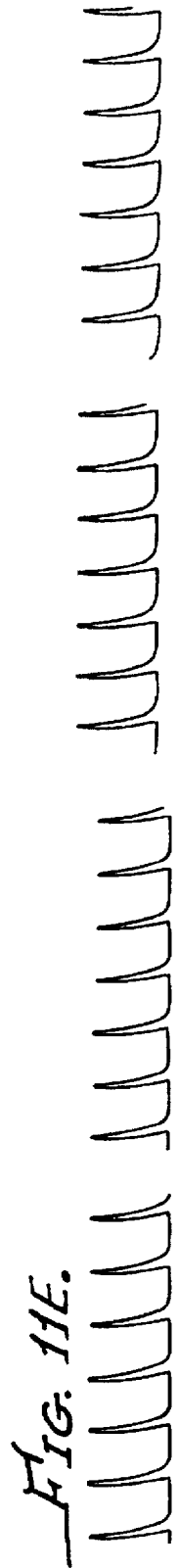
Figure 12A:
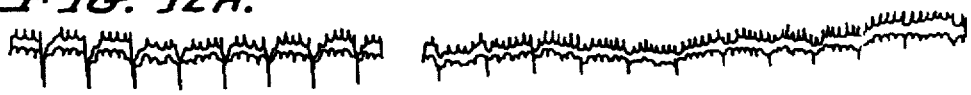
FIGS. 12A–12D show intramuscular injections of erabutoxin-b and vesamicol with the top left panel showing injection of erabutoxin-b at 0.1 mg and vesamicol at 1 mg being injected simultaneously into the muscle shown in the lower trace D, blood pressure, trace A, vagal responses, trace B also being shown, the top right panel showing a second dose of vesamicol at 1 mg injected 1 hour after the combination injection and further injections of vesamicol 1 mg made at hourly intervals, bottom left and center traces and the bottom right panel showing the block achieved at 1½ hours after the initial injections and after injection of three doses 1, 2, and 2 mg between the center bottom and the right bottom panels.
Figure 12B:
Figure 12C:
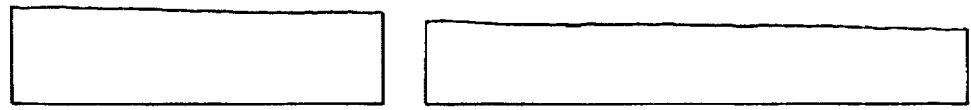
Figure 12D:
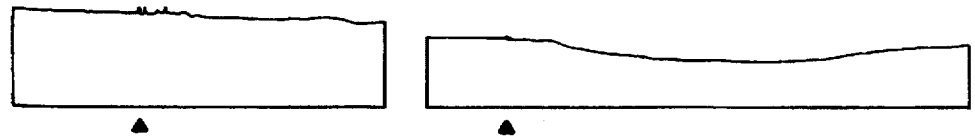
Figure 12A:
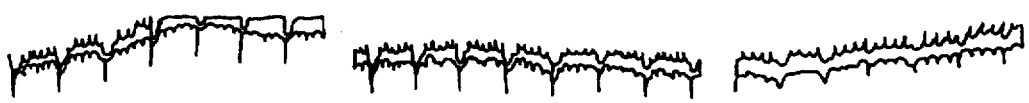
Figure 12B:
Figure 12C:
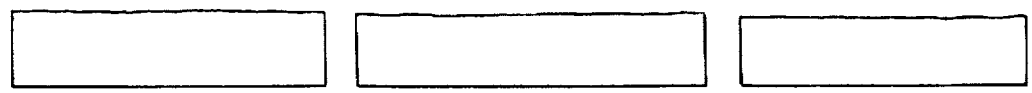
Figure 12D:
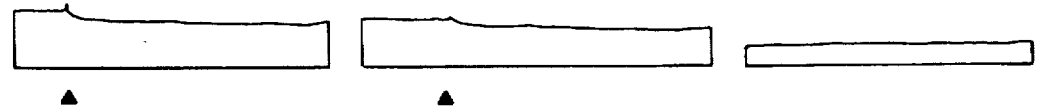

The result with erabutoxin-b and tetanic stimulation was not entirely unexpected. Although reversible competitive nicotinic antagonists produce marked tetanic fade, the phenomenon, at least in in vitro experiments is not usually seen with snake α-toxins. As stated previously, it is known that the action of vesamicol is revealed at 1 Hz stimulation frequency. However, all the previous experiments with erabutoxin-b had been carried out at 0.1 Hz. Thus, one experiment was carried out to assess the effects of the toxin at 1 Hz. In this experiment erabutoxin-b (0.2 mg i.m.) produced a block of around 50% after 100 minutes exposure (FIGS. 9 and 10). This compares with the 30–40% block (n=3) seen in the experiments performed at 0.1 Hz.

It is therefore concluded that 1 Hz stimulation is suitable for detecting the effects of both erabutoxin-b and vesamicol. Accordingly, subsequent experiments were carried out at the 1 Hz continuous stimulation.

Effects of combinations of erabutoxin-b and vesamicol

Given the ability of erabutoxin-b to produce a longer lasting but slowly developing block compared to vesamicol the ability of vesamicol to produce a more rapid onset block, and given the different sites of action of the two drugs, combinations of the two were considered.

Three pilot experiments were conducted, two at 1 Hz and one at 0.1 Hz. In the first, at 1 Hz, erabutoxin-b was injected at 0.1 mg i.e. half the dose used in the previous experiments with erabutoxin-b alone. Only a very slight blocking action was seen in the injected muscle (FIG. 11). Vesamicol (1 mg) was injected 20 minutes after the injection of erabutoxin-b, producing an 80–90% reduction of twitch tension (FIG. 11). The block then plateaued for 30 minutes before recovery (FIG. 11). A second injection of vesamicol (1 mg) produced almost identical effects. No evidence of spillover of the drugs into the general circulation was observed. The plateau phase of the neuromuscular block seen in this experiment was of interest. The twitch tension remained remarkably constant during this plateau, the responses resembling maximal twitches in their consistency. Although there was no immediately obvious way to test the hypothesis, that the twitches remaining may not have emanated from the tibialis muscle itself, but from one of the underlying, non-injected muscles in the same muscle group e.g. the flexor hallucis longus. The characteristics of the time course of the block, with an abrupt flattening of the onset phase when the plateau was reached, and an almost equally abrupt conversion from plateau to recovery phase, supported this conjecture. Thus it is possible that vesamicol was producing complete block of the tibialis muscle itself after pretreatment with erabutoxin-b, leaving a closely proximal muscle unaffected.

The two remaining pilot experiments were carried out injecting erabutoxin-b and vesamicol simultaneously. In the first, at 0.1 Hz, an immediate block was produced, with no spillover effect. The block then deepened slowly over a period of several hours. A second injection of vesamicol enhanced the block slightly but subsequent vesamicol injections were without effect.

In the final pilot experiment a slow onset block was produced by the simultaneous injection of the two drugs (FIG. 12). Subsequent "top-up" injections of vesamicol produced relatively slow onset (7 minutes to maximum effect) additional blocks that were consistent with its effects on ACh transport rather than with its local anaesthetic action. In this experiment the "plateau effect" described above was observed again with a top-up dose of vesamicol that produced a large additional block.

On the basis of these pilot experiments a quantitive evaluation of the effects of combination dosing was undertaken in cats. In these experiments both tibialis anterior muscles were stimulated at 1 Hz; one was used for intramuscular injection of drugs and the second for equal volume simultaneous saline controls. After stabilization of twitch tension, erabutoxin-b (0.1 mg) was injected at time zero, followed by two injections of vesamicol (1 mg) at 20 minutes and 40 minutes. The resultant block was monitored for 4 hours. One cat died after 75 minutes and results thereafter represent results from 5 animals. Results are expressed as percentage reduction from control in the drug injected muscle, and also corrected for reduction in tension in the saline injected muscle.

Responses were measured at 2 minute intervals for the first 80 minutes after erabutoxin-b administration, and subsequently at 20 minute intervals thereafter. The results are shown in graphical form.

Figure 13:
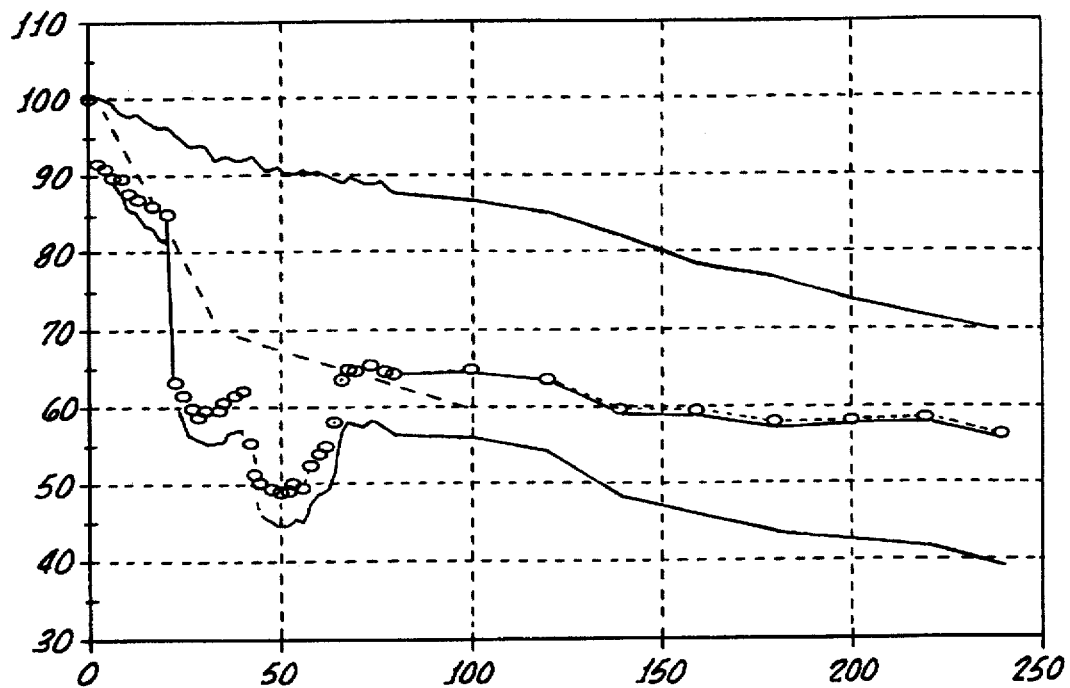
FIG. 13 is a plot showing a quantitative evaluation of a block produced by a combination of erabutoxin-b and vesamicol with the time/inhibition plot showing percentage control twitch tension on the vertical axis and time in minutes on the horizontal axis, the curves represent the mean of six experiments in which a time zero erabutoxin-b at 0.1 mg was injected into one tibialis muscle followed by two injections of vesamicol 1 mg at 20 and 40 minutes, respectively, the bottom line showing the twitch depression in the injected muscle, the top line showing the depression in the saline injected control muscle and the middle line representing the neuromuscular block corrected for the saline control effects.
Figure 14:
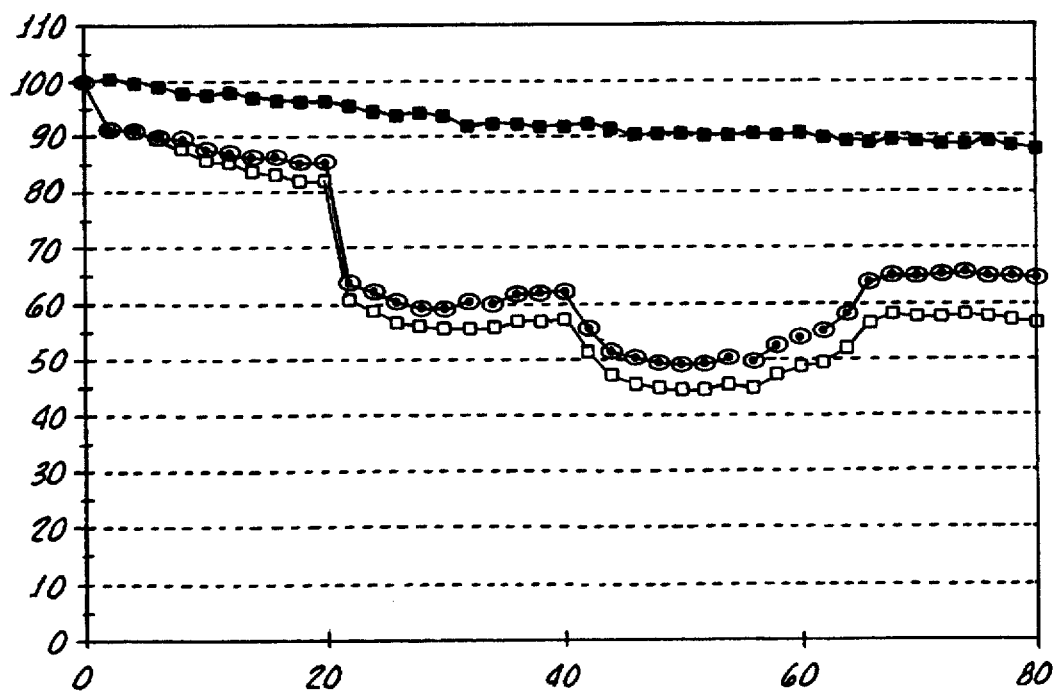
FIG. 14 is a time/inhibition plot similar to FIG. 13 in which the time base is extended to cover a 4 hour administration period, after 15 minutes the data represents results from five cats and the dotted line showing the superimposed data from one experiment carried out with erabutoxin-b at 0.2 mg alone at the same stimulation frequency.

In these experiments erabutoxin-b produced an initial 10% drop in twitch tension immediately after injection, followed by a very gradual deepening of the block in the injected muscle to around 15% after 20 minutes (FIGS. 13 and 14). The first injection of vesamicol rapidly deepened the block to 40%, continued to slowly deepen to 45% over the next 10 minutes, and then to slowly recover. The second injection of vesamicol took place when the block had recovered almost to 40%. This secondary injection produced a less precipitous block than that of the first injection, the block reading 55% in 10 minutes before recovery commenced. Recovery from the effects of vesamicol proceeded for a further 20 minutes before the overall block began to re-develop, presumably due to the increasing effects or erabutoxin-b with time. The block then continued to deepen over the next 3 hours in the injected muscle.

When the responses in the injected muscle were corrected for the effects of the very gradual reduction in tension in the saline control injected muscle, an essentially similar picture to that described above emerged (FIGS. 13 and 14). However, the block seen after 70–80 minutes, when the vesamicol effects had apparently worn off, was seen to develop only at a very slow rate (less than 10% over 2½–3 hours) after correction.

The anaesthetized cat model described appears to be a useful system for investigating neuromuscular block produced by intramuscularly injected drugs which are suitable in the administration of botulinum toxin as hereinabove described. The model has been used to show that local injections of reversible competitive neuromuscular blocking drugs (such as vecuronium) produce small effects which are not dose-related. Injections of larger doses of these drugs appear to lead to spillover of the compound into the general circulation.

In contrast, intramuscular injections of erabutoxin-b, an irreversible competitive nicotinic antagonist, produced a slowly-developed and long-lasting neuromuscular block with no spillover into the general circulation. In contrast, intramuscular injections of erabutoxin-b, an irreversible competitive nicotinic antagonist, produced a slowly-developed and long-lasting neuromuscular block with no spillover into the general circulation.

Finally, local injections of vesamicol, an inhibitor of vesicular acetylcholine storage, produced a rapidly-developed and short-lived neuromuscular block. Simultaneous local injections of erabutoxin-b and vesamicol produced a considerable neuromuscular block with no spillover. Vesamicol enhanced the erabutoxin-b neuromuscular block, however, its effects were still fairly short-lived and its simultaneous injection did not appear to affect the subsequent long-term neuromuscular block produced by erabutoxin-b. It should be appreciated that the "long-term" block by erabutoxin-b, measured in hours is in effect short compared to the effect of botulinum toxin when it is measured in weeks as hereinabove described.

Although there has been hereinabove described a specific method for the administration of botulinum toxin and the selection of neuromuscular agents suitable for such administration, in accordance with the present invention, for purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for administration of botulinum toxins into muscles experiencing hyperactivity due to a neuromuscular disorder, said method comprising the steps of:
    (a) selecting at least one neuromuscular blocking agent having a duration of activity shorter than neuromuscular blocking activity of botulinum toxin;
    (b) selecting at least one muscle of a muscle group;
    (c) intramuscularly injecting the selected agent into the selected muscle;
    (d) observing muscle relaxation in both the selected muscle and other nonselected muscles in the muscle group to determine spill-over, muscle tone and balance;
    (e) repeating steps (b)–(d) until a final muscle selection is found; and
    (f) intramuscularly injecting botulinum toxin into the final muscle selection.

2. The method according to claim 1 wherein the at least one neuromuscular blocking agent is selected from Table 1.

3. The method according to claim 1 wherein the at least one neuromuscular blocking agent comprises vecuronium.

4. The method according to claim 1 wherein the at least one neuromuscular blocking agent comprises erabutoxin -b.

5. The method according to claim 1 wherein the at least one neuromuscular blocking agent comprises vecuronium and erabutoxin -b.

6. The method according to claim 1 wherein the at least one neuromuscular blocking agent comprise a snake α-neurotoxin.

7. The method according to claim 1 wherein the step of selecting at least one neuromuscular blocking agent comprises the steps of:
    i) stimulating a group of muscles in a laboratory animal with electrical pulses to induce spasm therein;
    ii) intramuscularly injecting a selected muscle of the muscle group of the laboratory animal with a prepared agent;
    iii) observing reduction in spasm of the injected selected muscle of the laboratory animal;
    iv) observing reduction in spasm of a nonselected muscle of the muscle group of the laboratory animal; and
    v) comparing the observations made in steps (iii) and (iv).

8. A method for administration of botulinum toxin into muscles having muscular spasm, said method comprising the steps of:
    (a) selecting at lest one muscle of a muscle group;
    (b) intramuscularly injecting at least one neuromuscular blocking agent into the selected muscle, the agent having a duration of activity shorter than neuromuscular blocking activity of botulinum toxin in the selected muscle;
    (c) observing muscle relaxation in both the selected muscle and other nonselected muscles in the muscle group to determine spill-over, muscle tone and balance;

(d) repeating steps (a)–(c) until a final muscle selection is found; and (e) intramuscularly injecting botulinum toxin into the final muscle selection.

9. The method according to claim 8 wherein the at least one neuromuscular blocking agent is selected from Table 1.

10. The method according to claim 8 wherein the at least one neuromuscular blocking agent comprises vecuronium.

11. The method according to claim 8 wherein the at least one neuromuscular blocking agent comprises erabutoxin -b.

12. The method according to claim 8 wherein the at least one neuromuscular blocking agent comprises vecuronium and erabutoxin -b.

13. The method according to claim 8 wherein the at least one neuromuscular blocking agent comprise a snake α-neurotoxin.

14. A method for assaying neuromuscular blocking activity of an agent suitable for enhancing effectiveness of botulinum toxin injection for the treatment of muscle spasm, the method comprising the steps of:

(a) stimulating a group of muscles with electrical impulses to induce spasm therein;

(b) intramuscularly injecting a selected muscle of the muscle group with a selected agent;

(c) observing reduction in spasm of the injected selected muscle;

(d) observing reduction in spasm of a nonselected muscle of the muscle group; and (e) comparing the observations made in steps (c) and (d).

15. The method according to claim 14 wherein the step of stimulating a group of muscles comprises stimulating the group at a rate of between about 0.1 Hz to about 200 Hz.

16. The method according to claim 15 wherein the step of stimulating a group of muscles further comprises stimulating the muscle group with rectangular pulses of about 0.2 ms duration and a strength sufficient to produce maximal spasm.

17. The method according to claim 14 wherein the step of intramuscularly injecting a selected muscle comprises injecting a tibialis anterior muscle.

18. The method according to claim 16 wherein the step of observing reduction in spasm of a nonselected muscle comprises observing reduction in spasm of an ipsilateral soleus muscle.

* * * * *